(12) United States Patent
Funk

(10) Patent No.: US 9,173,621 B2
(45) Date of Patent: Nov. 3, 2015

(54) METHOD AND APPARATUS FOR ADAPTIVE X-RAY FILTRATION

(71) Applicant: TRIPLE RING TECHNOLOGIES, INC., Newark, CA (US)

(72) Inventor: Tobias Funk, Martinez, CA (US)

(73) Assignee: Triple Ring Technologies, Inc., Newark, CA (US)

( * ) Notice: Subject to any disclaimer, the term of this patent is extended or adjusted under 35 U.S.C. 154(b) by 195 days.

(21) Appl. No.: 13/931,553

(22) Filed: Jun. 28, 2013

(65) Prior Publication Data

US 2014/0294139 A1 Oct. 2, 2014

Related U.S. Application Data

(60) Provisional application No. 61/807,704, filed on Apr. 2, 2013.

(51) Int. Cl.
| | |
|---|---|
| *A61B 6/00* | (2006.01) |
| *G21K 1/04* | (2006.01) |
| *A61B 6/03* | (2006.01) |
| *G21K 1/10* | (2006.01) |
| *A61B 6/06* | (2006.01) |

(52) U.S. Cl.
CPC . *A61B 6/035* (2013.01); *A61B 6/06* (2013.01); *A61B 6/4035* (2013.01); *G21K 1/043* (2013.01); *G21K 1/10* (2013.01)

(58) Field of Classification Search
CPC ........ A61B 6/032; A61B 6/035; A61B 6/405; A61B 6/4035; G21K 1/04; G21K 1/043; G21K 1/10; G21K 1/046
See application file for complete search history.

(56) References Cited

U.S. PATENT DOCUMENTS

| | | | | |
|---|---|---|---|---|
| 6,968,030 | B2 * | 11/2005 | Hoffman | 378/5 |
| 7,046,756 | B2 * | 5/2006 | Hoffman | 378/5 |
| 7,068,750 | B2 * | 6/2006 | Toth et al. | 378/16 |
| 7,088,799 | B2 * | 8/2006 | Hoffman | 378/5 |
| 7,308,073 | B2 * | 12/2007 | Tkaczyk et al. | 378/16 |
| 7,474,736 | B2 * | 1/2009 | Munro et al. | 378/159 |
| 8,873,704 | B2 * | 10/2014 | Stierstorfer | 378/16 |
| 2003/0086534 | A1 * | 5/2003 | Seufert | 378/150 |
| 2003/0198319 | A1 | 10/2003 | Toth et al. | |
| 2004/0234021 | A1 * | 11/2004 | Hoffman | 378/4 |
| 2004/0234037 | A1 * | 11/2004 | Hoffman | 378/156 |
| 2005/0089135 | A1 * | 4/2005 | Toth et al. | 378/16 |
| 2005/0243971 | A1 * | 11/2005 | Hoffman | 378/156 |
| 2006/0072705 | A1 * | 4/2006 | Munro et al. | 378/159 |
| 2007/0092066 | A1 * | 4/2007 | Tkaczyk et al. | 378/156 |
| 2011/0204260 | A1 | 8/2011 | Ein-Gal | |
| 2012/0219106 | A1 * | 8/2012 | Stierstorfer | 378/15 |
| 2014/0294139 | A1 * | 10/2014 | Funk | 378/16 |

* cited by examiner

*Primary Examiner* — Thomas R Artman
(74) *Attorney, Agent, or Firm* — Sabrina N. David; Joseph T. Lin

(57) ABSTRACT

The present invention pertains to a system and method for adaptive X-ray filtration comprising a volume of X-ray attenuating material with a central less attenuating three-dimensional region. The volume of X-ray attenuating material can be positioned within 10 cm from an X-ray source and rotated around an internal axis of rotation. The volume of X-ray attenuating material can be symmetric around the internal axis while the central less attenuating region can be asymmetric around the internal axis. Rotating the volume by a predetermined angle around the internal axis can change the amount of attenuation of an X-ray beam through the filter. The volume can be rotated by the same predetermined angle as an imaging subject or X-ray source and detector are rotated during X-ray image acquisition.

17 Claims, 6 Drawing Sheets

METHOD AND APPARATUS FOR ADAPTIVE X-RAY FILTRATION

RELATED U.S. APPLICATION

The present invention claims priority to the provisional U.S. patent application No. 61/807,704, entitled "System and Method for Adaptive Bowtie Filtration,", filed Apr. 2, 2013, hereby incorporated by reference in its entirety.

FIELD OF THE INVENTION

The present invention is in the field of X-ray imaging. The present invention is also in the field of X-ray filters for computed tomography X-ray imaging.

BACKGROUND

Decreasing regional variations in exposure levels seen by an X-ray detector can yield improvements X-ray image quality; since a detector can be limited to a predetermined dynamic range, minimizing the difference between the most exposed and least exposed regions of the detector can improve its sensitivity to slight differences in exposure, e.g., the contrast, or avoid having saturated or completely dark regions in an image. It can be particularly difficult to control dynamic range in computed tomography (CT) applications due to the plurality of different projection images seen by the detector in a single scan. In CT, projection images can be acquired through more than 180 degrees around a patient, and the profile of a patient can be much narrower in some projections than others, e.g., narrower viewed from shoulder to shoulder than front to back. In narrow projections the detector may be highly exposed or over exposed, e.g., on the edges. Conversely, wide projections may receive a higher dose than necessary to penetrate the patient in that direction, as a patient may be thinner in a front to back orientation than in a side to side projection. Narrowing dynamic range in CT may both improve image quality and decrease patient X-ray dose.

One strategy that has been implemented to address dynamic range problems in CT is placement of a bowtie filter between an X-ray source and the patient during imaging. A bowtie filter has been a physical filter with a shape that is relatively thick near the edges and thin at its center, with a linear, parabolic, circular, or any other type of gradient between these maxima and minima Use of a bowtie filter can also provide benefits for patient X-ray dose reduction, which has been a goal of the medical imaging community over the past decades. Without use of the filter, achieving enough photons for adequate noise performance at the center of the detector, where in some projections the patient may be the thickest, may result in the outer regions of the detector receiving an unnecessarily large number of photons. This large number of photons may be detrimental to image quality any may also contribute to excess patient dose.

While bowtie filters can have many advantages, their utility is also limited by a lack of adaptability. For example, to accommodate a range of patient sizes, a set of bowtie filters of variety of sizes may be provided and the closest match can be selected for use with each patient. However, the closest match from a premade set may not be an exact or ideal match for each patient. The thickness of a patient profile also can vary with projection angle, such that a single bowtie filter cannot achieve optimal results at all projection angles throughout a CT scan of a patient. A limited number of relatively complex bowtie filters have been proposed for adaptive bowtie filtration. Examples include a piecewise-linear dynamic bowtie filter proposed by Hsieh et al. (Scott S. Hsieh; Norbert J. Pelc. "The feasibility of a piecewise-linear dynamic bowtie filter." Med. Phys. 40, 031910 (2013)), which utilizes a plurality of precisely controlled wedge-like pistons to implement piecewise triangular function and a dynamic bowtie filter comprising a pair of sliding wedges proposed by Szczykutowicz et al (Timothy P. Szczykutowicz; Charles Mistretta. "Intensity Modulated CT implemented with a dynamic bowtie filter." Proc. SPIE 8668, Medical Imaging 2013: Physics of Medical Imaging, 866818 (Mar. 19, 2013)).

Embodiments of the present invention can provide adaptive bowtie filtration with relatively simple and fast implementation methods and enhanced flexibility relative to existing systems.

SUMMARY

The present invention pertains to a system and method for adaptive X-ray filtration comprising a volume of X-ray attenuating material with a central less attenuating three-dimensional region. The volume of X-ray attenuating material can be positioned within 10 cm from an X-ray source and rotated around an internal axis of rotation. The volume of X-ray attenuating material can be symmetric around the internal axis while the central less attenuating region can be asymmetric around the internal axis. The volume of X-ray attenuating material can be a rotatable element such that attenuation of an X-ray beam through the filter is a function of the angular orientation of the rotatable element around the internal axis. Rotating the volume by a predetermined angle around the internal axis can change the amount of attenuation of an X-ray beam through the filter. The volume can be rotated by the same predetermined angle as an imaging subject or X-ray source and detector are rotated during X-ray image acquisition.

The rotatable element can be a cylinder, and the less attenuating central region may be an elliptic cylinder or cone or may have an elliptic cross section. Cross sectional dimensions of the less attenuating central region may vary with height of the three-dimensional volume. The less attenuating central region may be hollow. The less attenuating central region can also be a miniaturized shape of the imaging subject or otherwise tailored to a predetermined imaging subject. The rotatable element can include aluminum or iron. Properties of the rotatable element can be adjusted prior to imaging based on a preliminary measurement of the imaging subject. A stationary filter element can also be provided and conform to outer edges of the rotatable element to equalize distances of X-ray beam paths through the filter.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Figure 1:
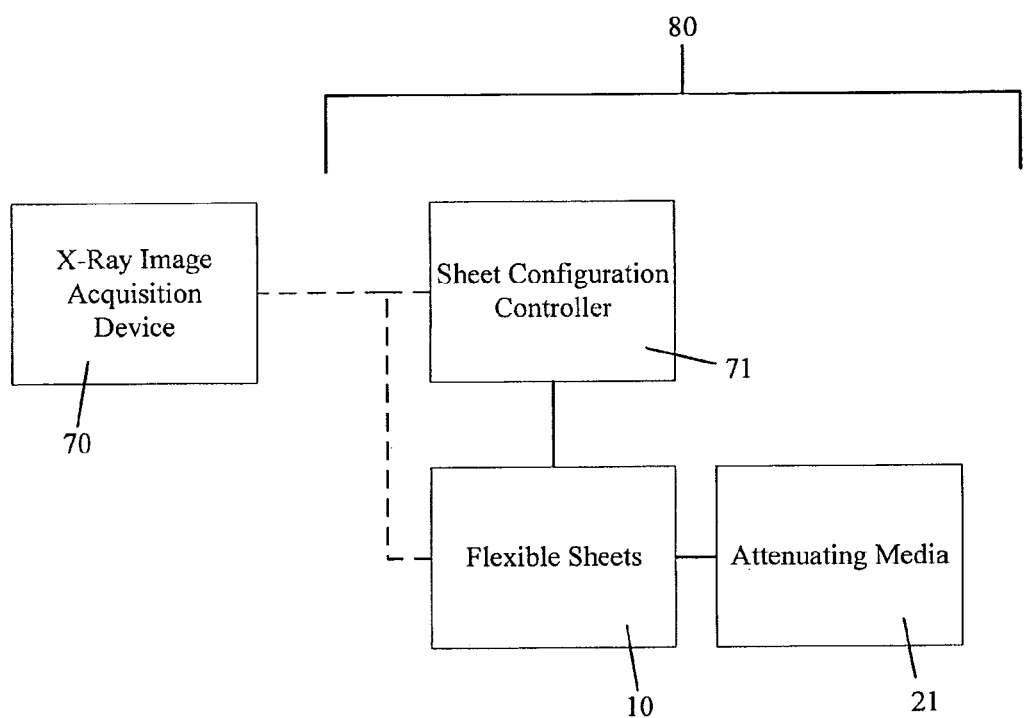
FIG. 1 is a diagram representing components of an adaptive X-ray filter of one embodiment of the present invention.

FIG. 1 is a diagram representing components of an adaptive X-ray filter of one embodiment of the present invention. An adaptive X-ray filter 80 can comprise one or more flexible sheets 10, an attenuating media 21, and a sheet shape controller 71 for controlling aspects of flexible sheets 10. Attenuating media 21 may be coupled to flexible sheets 10, e.g., in a manner such that changes in aspects of flexible sheet 10 affect the spatial distribution of attenuating media 21. Adaptive X-ray filter 80 can be coupled to an X-ray image acquisition device 70, for example by being attached to an X-ray source or gantry, or in any space in the X-ray beam path between a source and detector or between a source and the imaging subject. Adaptive filter 80 can be positioned relative to X-ray image acquisition device 70 such that controlling aspects of flexible sheets 10 can affect the spatial distribution of attenuating media 21 in the X-ray beam path. For example, increasing the amount, e.g., thickness, of attenuating media in the beam path in a predetermined region of the beam path can increase the attenuation of said region of the beam, e.g., decrease the intensity of the beam in that region.

Attenuating media 21 may comprise attenuating particles, including but not limited to microparticles or nanoparticles of an attenuating material or materials. Attenuating materials may have an atomic number greater than or equal to 12. For example, such particles can comprise without limitation lead, gold, rhenium, silver, tungsten, niobium, cadmium, bismuth, thallium, iridium, copper, aluminum, iron, or palladium particles, or any other similar materials or alloys thereof. In one embodiment of the present invention, a concentration of attenuating particles can be very high, e.g., such that particles are contacting one another. In this embodiment, a gel, fluid, or similar lubricant may be provided for decreasing friction between particles, e.g., when sliding past one another to conform to different filter states. In another embodiment of the present invention, the concentration of attenuating particles can be lower, with particles being suspended in a gel, fluid, or similar medium. Gels or fluids in the attenuating media of embodiments of the present invention can comprise without limitation any physical gel, chemical gel, hydrogel, organogel, xerogel, or other natural or synthetic gel or fluid.

Sheets 10 can be made of any pliable or semi-pliable materials, including but not limited to metals, alloys, plastics, polymers, or any other materials. In one embodiment of the present invention, sheets 10 can comprise stainless steel. Sheet shape controller 71 may comprise one or more motors, stepper motors, linear actuators, hydraulic or pneumatic actuators, worm drives, encoders, and any other mechanical or electrical components or combinations thereof. Sheet shape controller 71 may further comprise computing or processing capabilities, including without limitation a processor, microprocessor, controller, microcontroller, logic chip, or any similar device or connection to an external platform.

Figure 2A:
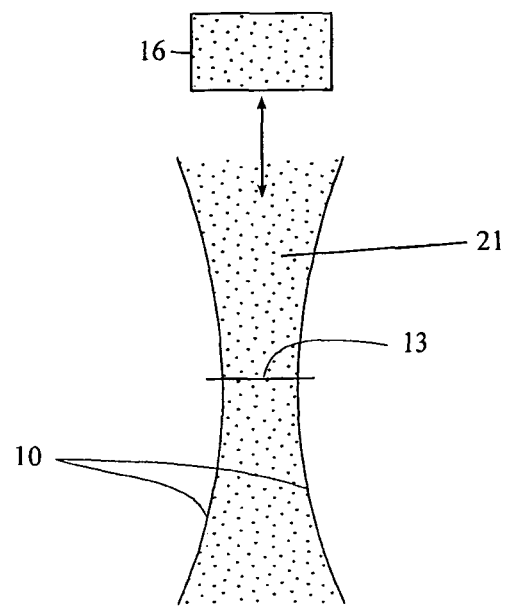
FIG. 2A is a diagram representing an adaptive filter of one embodiment of the present invention in one possible shape.
Figure 2B:
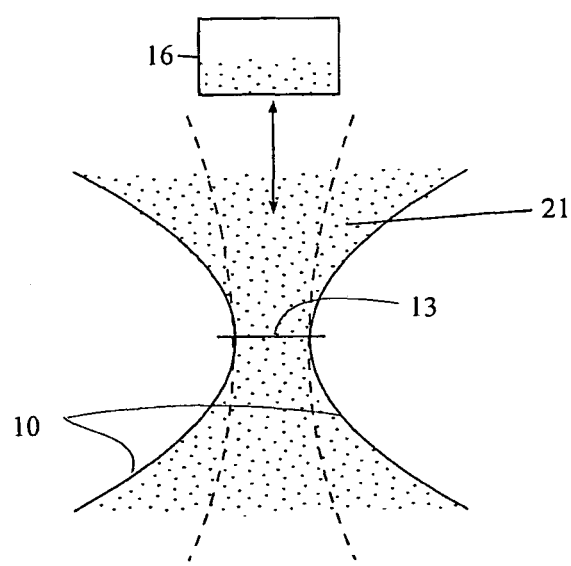
FIG. 2B is a diagram representing another possible shape of the adaptive filter of the embodiment of FIG. 2A.

FIG. 2A is a diagram representing an adaptive filter of one embodiment of the present invention in one possible shape. A set of flexible sheets 10 can control the distribution of an attenuating inner media, e.g., in the path of an X-ray beam. FIG. 2B is a diagram representing another possible shape of the adaptive filter of the embodiment of FIG. 2A. In FIG. 2B, the shape of FIG. 2A is indicated with dashed lines while and a second shape is shown with solid lines. In the embodiment of FIGS. 2A and 2B flexible sheets 10 may be configured to bend, bow, or otherwise conform to a variety of shapes, including but not limited to those shown in the two figures.

In the embodiment of FIG. 2A, a separator 13 is shown connecting sheets 10. Separator 13 can maintain a fixed separation between center points of sheets 10. When pressure is applied, some regions of sheets 10 may move outward, increasing the distance between sheets 10 at many points while maintaining separation at the sheets' centers. However, in other embodiments separator 13 may be omitted. A variety of shapes are possible and may be tailored to allow the distance between sheets 10 to increase, decrease, or stay the same at predetermined points. In embodiments comprising a fixed distance between a center point of the flexible sheets, e.g., a separator 13 as shown in the embodiment of FIG. 2A, said fixed distance can be between 0 cm and 2 cm, inclusive.

Attenuating media can be contained between sheets 10 in one of a variety of manners. In the embodiment of FIG. 2A and FIG. 2B, an outer reservoir 16 may be provided. Reservoir 16 may store supplemental or overflow amounts of attenuating media. For example, in a transition between the shapes of FIG. 2A and FIG. 2B, attenuating media may flow into reservoir 16. In a transition between the second state and first state, attenuating media may flow out of reservoir 16 to fill in volume between sheets 10. An orifice, pipe, or other feature may be provided to allow attenuating media 21 to flow between flexible sheets 10 and reservoir 16.

As previously described, distance between the outer sheets may be selectable or variable, e.g., if contacts with outer housing are variable or sliding points of contact, or may be fixed. A wider distance between outer sheets can accommodate a greater amount of attenuating media, which may be useful, for example, for imaging relatively larger patients. In one embodiment of the present invention, the concentration of attenuating particles in the inner attenuating matter can be selected prior to each imaging situation. For example, the attenuation properties of an imaging subject can be determined, and a custom gel can be created and inserted into the filter reservoir. In this embodiment, the filter apparatus can further comprise a cleaning or washing mechanism configured to clean or wash gel out of the filter once imaging has been completed.

Figure 3A:
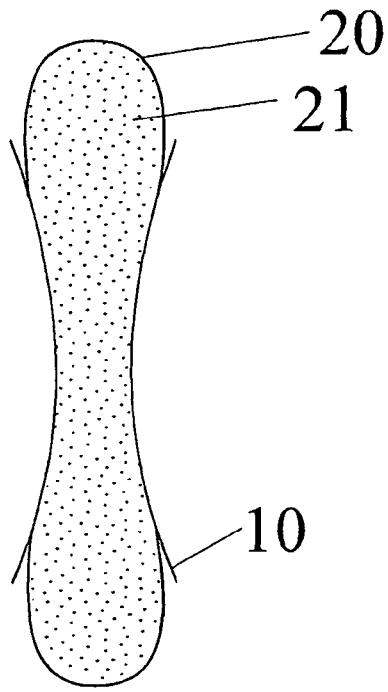
FIG. 3A is a diagram showing one shape of an embodiment of the present invention wherein attenuating media is contained in a bag or supplementary vessel.
Figure 3B:
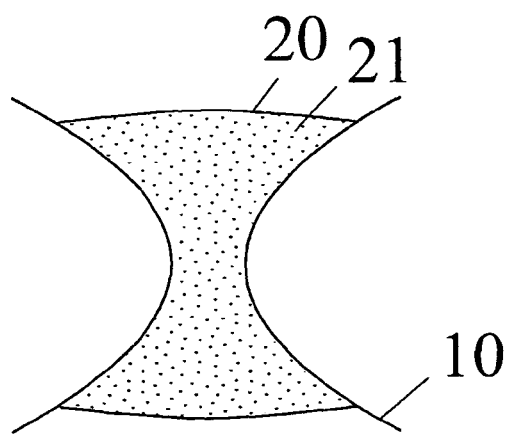
FIG. 3B is a diagram showing another shape of an embodiment of the present invention wherein attenuating media is contained in a bag or supplementary vessel.

FIG. 3A and FIG. 3B are diagrams showing an embodiment of the present invention wherein attenuating media is contained in a bag or supplementary vessel. The bag or vessel can be fixed at points to each of the flexible sheets. As shown in FIG. 3A and FIG. 3B, in this embodiment attenuating media 21 in a vessel 20 may adapt to changes in distances between sheets 10 without use of an outer reservoir or flow of the media. When the distances, e.g., volume, between sheets 10 are relative small, attenuating media can be stored outside of the imaging path, as shown in FIG. 3A. When distances between sheets 10 are widened, vessel 20 and attenuating media 21 can be pulled back into the imaging path and can increased the attenuation of the filter. Vessel 20 can be attached to predetermined points or along the lengths of sheets 10 with any type of adhesives, fastening mechanisms, or combinations thereof.

In embodiments that have been described and similar embodiments of the present invention, the thickness of each of flexible sheets containing attenuating media, e.g., the thickness of each of sheets 10, can be between 100 μm and 5 mm. The thickness of each of the sheets can further be between 100 μm and 500 μm, 500 μm and 1 mm, 1 mm and 1.5 mm, 1.5 mm and 2 mm, 2 mm and 3 mm, or 3 mm and 5 mm, inclusive, and any other integer or non-integer number of micrometers or millimeters within or between the enumerated ranges. An uncompressed length of sheets 10 may be between 1 cm and 20 cm, inclusive. Sheets may also have an uncompressed length between 1 cm and 15 cm, 1 cm and 10 cm, 1 cm and 9 cm, 1 cm and 8 cm, 1 cm and 7 cm, 1 cm and 6 cm, or 1 cm and 5 cm, inclusive, and any integer or non-integer number of centimeters within or between the enumerated ranges.

During CT and other applications, sheets of embodiments of the present invention may be compressed up to 70% of their uncompressed height. Amounts of compression implemented during the application can be tailored to the width of the imaging subject from different projection angles. The amount of compression implemented during a scan can further be between 60% and 70%, 50% and 60%, 40% and 50%, 30% and 40%, or 1% and 30%, inclusive, and any integer or non-integer percentage within or between the enumerated ranges.

Figure 4A:
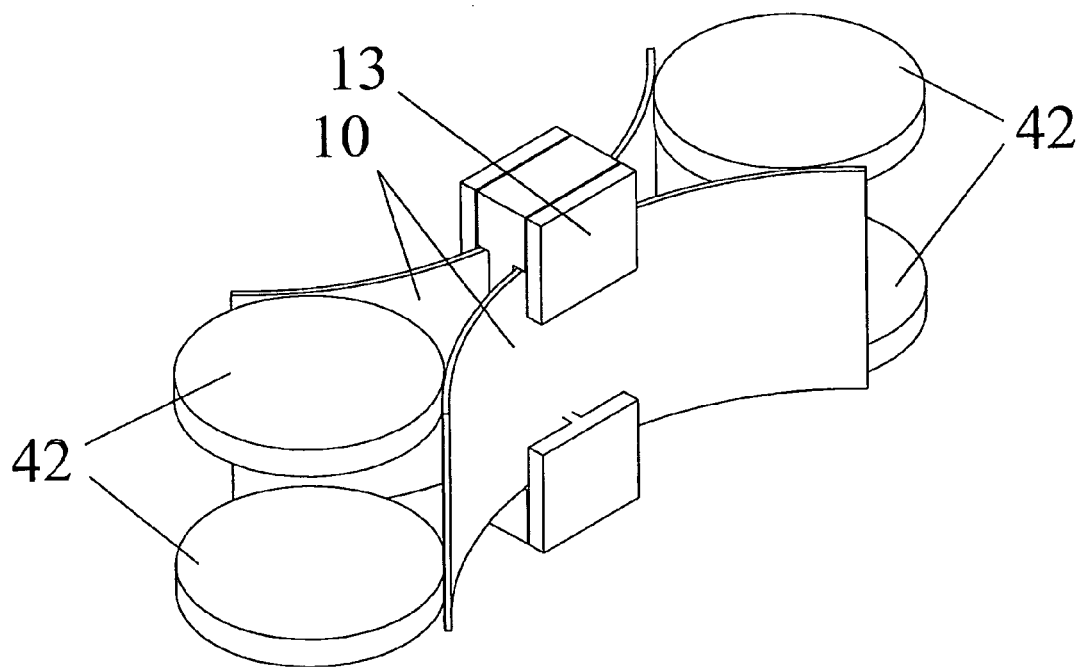
FIG. 4A is a diagram representing another configuration for control of the flexion of a pair of flexible sheets in an adaptive filter of one embodiment of the present invention.
Figure 4B:
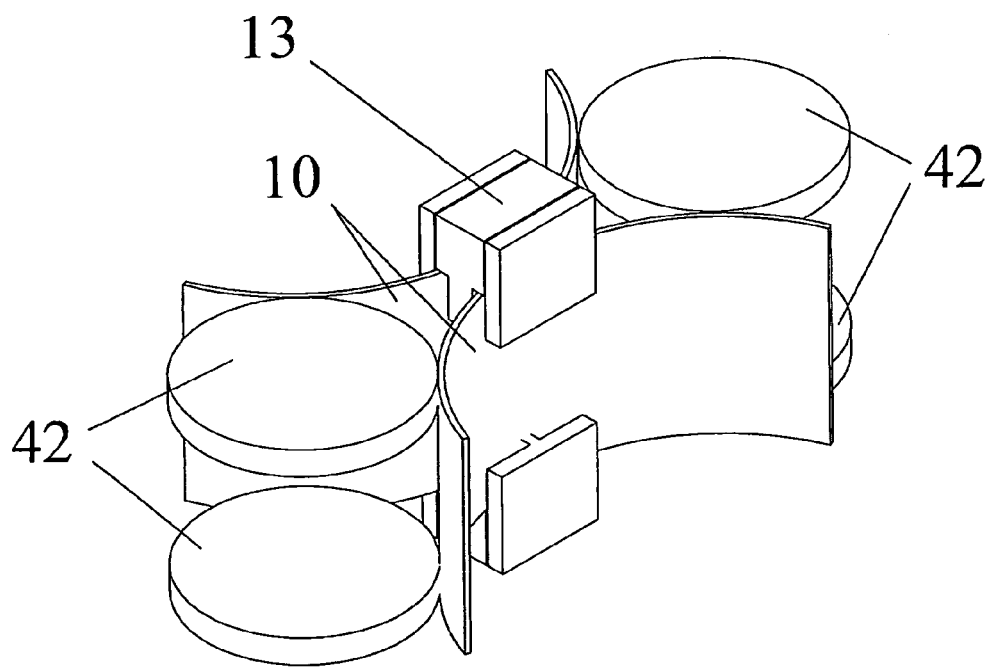
FIG. 4B is a diagram representing the configuration of FIG. 4A in a state with increased flexion of the sheets.

FIG. 4A is a diagram representing another configuration for control of the flexion of a pair of flexible sheets in an adaptive filter of one embodiment of the present invention. In this embodiment separator 13 may comprise a pin or beam as previously described or edge-based separators as illustrated in the figure. Attenuating media may be contained in a vessel as described with respect to FIGS. 3A and 3B and is not illustrated here. The flexion of sheets 10 may be controlled by one or more sets disks 42 positioned between sheets 10 such that sliding disks 42 toward separator 13 can increase the flexion of sheets 10 and sliding disks 42 away from separator 13 can decrease the flexion of sheets 10. FIG. 4B is a diagram representing the configuration of FIG. 4A in a state with increased flexion of the sheets. Sheets 10 can be configured to bow as illustrated in FIG. 4B as disks 42 are slid inward, e.g., toward separator 13. The position of disks 42 can be controlled with any mechanism, including but not limited to linear slides, stepper motors, or any other electronic or mechanical actuators, motors, or controllers.

In one embodiment of the present invention, an adaptive X-ray filter can comprise a rotating element positioned in the X-ray beam path, wherein rotation of the element around an internal axis can alter the amount and spatial pattern of attenuation of the X-ray beam. The adaptive filter can also comprise stationary elements in addition to the rotating element. The construction, shape, internal features, or other aspects of the rotating element in this embodiment can be tailored to predetermined attenuation characteristics of the imaging subject. For example, in one embodiment, a rotating filter element can comprise a cylinder, block, sphere, or other three-dimensional volume of an attenuating material, in which a central region can be hollow or filled with a less attenuating material. The shape of the hollow or less attenuating region can be tailored to predetermined attenuation characteristics of the imaging subject, e.g., including but not limited to a miniaturized shape of the imaging subject or an attenuation map of the imaging subject. For example, the dimensions of a hollow or less attenuating region in a predetermined cross section can be a function or inverse function of an attenuation map of the imaging subject for that cross section.

The attenuating material of such embodiments can include, without limitation, iron, aluminum, and any alloys or combinations thereof. The attenuating material may also include any material having at atomic number between 12 and 80, inclusive. As previously described, a hole or cavity in this material can be hollow or may be filled with a less attenuating material, which may be any material having an atomic number lower than the attenuating material, including but not limited to a material with an atomic number less than 40, 26, 20, or 13.

Figure 5A:
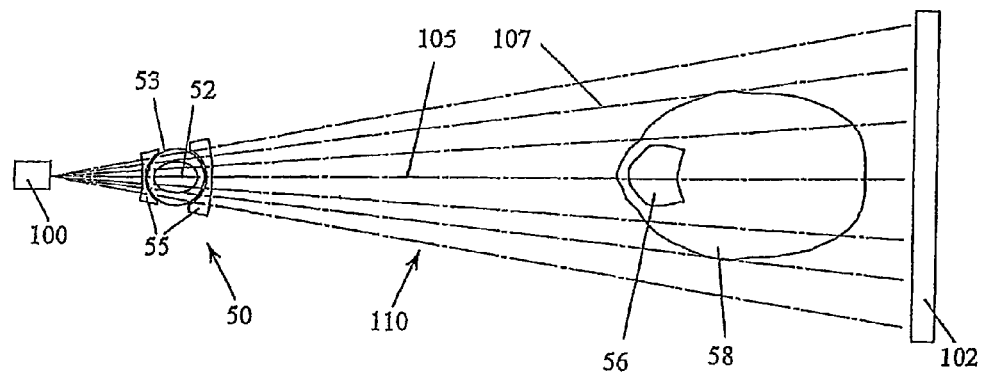
FIG. 5A is a diagram representing an adaptive filter having a rotating element of one embodiment of the present invention.

FIG. 5A is a diagram representing an adaptive filter having a rotating element of one embodiment of the present invention. The embodiment of FIG. 5A may be utilized for X-ray imaging, e.g., computed tomography imaging, of a human head. An exemplary cross section 58 of a human head is shown, e.g., for explanation, and which in the configuration of FIG. 5A may represent the head facing an X-ray source 100. A filter 50 of this embodiment can comprise a rotatable element 53 having a hollow or less attenuating region 52 within it. In one embodiment, rotatable element 53 can be a cylinder, e.g., a solid cylinder of an attenuating material with the exception of a hollowed region 52 within it. In the embodiment of FIG. 5A, hollowed or less attenuating region 52 may have a cross section with a shape similar to the shape of head cross section 58. Hollowed or less attenuating region 52 may, for example, have an elliptical cross section or comprise a hollow elliptic cylinder within rotatable element 53. Stationary filter elements 55 may also be provided and may accommodate rotation of rotatable element 53, e.g., while equalizing the length of paths of each of X-rays 110 through filter 50. Stationary filter elements 55 may comprise an attenuating material, e.g., a material having an atomic number greater than 39, and may optionally be the same material as rotatable element 53.

X-rays 110 can be emitted by X-ray source 100 and detected by an X-ray detector 102. In this embodiment, adaptive filter 50 can be configured to more greatly attenuate those of X-rays 110 that are not attenuated or attenuated relatively little by the imaging subject, e.g., have relatively short paths through head cross section 58. As illustrated in FIG. 5A, central ray 105 may travel the longest path through head cross section 58. Filter 50 may be configured such that central ray 105 travels through the least attenuating path through rotatable element 53 and stationary elements 55, e.g., the longest path through hollow region 52. In this configuration an outer ray 107 that travels a very short path through head cross section 58 can be aligned with a more attenuating path through filter 50, e.g., through attenuating material in rotatable element 53 and stationary elements 55.

Figure 5B:
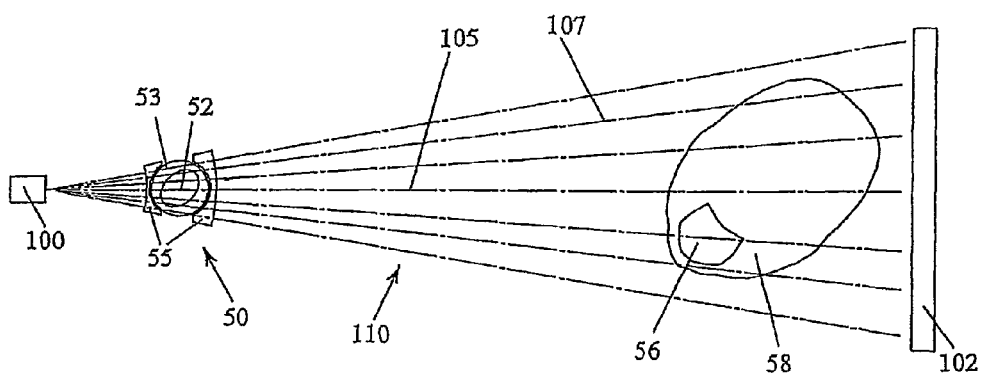
FIG. 5B is a diagram representing the adaptive filter of the embodiment of FIG. 5A in a second orientation.

X-ray source 100 and X-ray detector 102 may be rotated around the imaging subject, e.g., for computed tomography or other imaging applications, changing the orientation of the imaging subject relative to the source and detector. FIG. 5B is a diagram representing the adaptive filter of the embodiment of FIG. 5A in a second orientation. In FIG. 5B, rotatable element 53 can be rotated by an amount corresponding to the rotation of head cross section 58 relative to X-ray source 100 and X-ray detector 102. Rotation of rotatable element 53 can change the distribution of attenuating material in the paths of X-rays 110, e.g., relative to FIG. 5A. For example, it can be seen that in the orientation of FIG. 5B central ray 105 can travel a less attenuating path through filter 50 compared to the path of central ray 105 through filter 50 in the orientation of FIG. 5A. The decrease in filter attenuation can be related to the increase in attenuation by the imaging subject; it can also be seen that the path of central ray 105 through head cross section 58 can be longer, e.g., more attenuating, in the orientation of FIG. 5B than in the orientation of FIG. 5A.

Figure 5C:
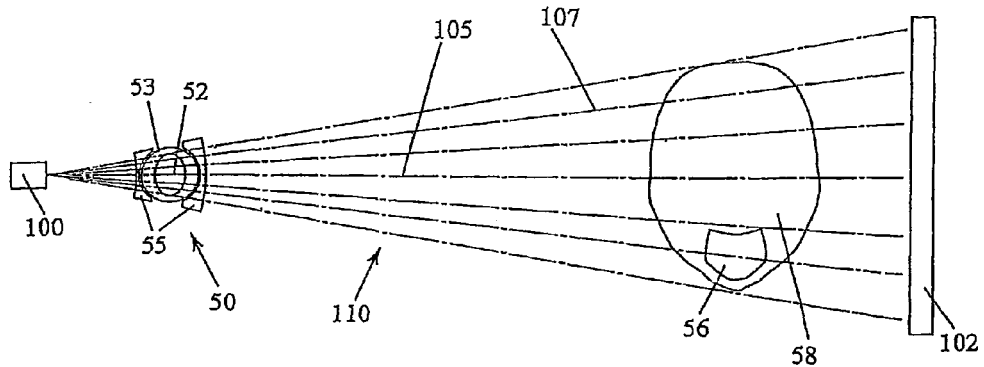
FIG. 5C is a diagram representing another orientation of the filter of the embodiment of FIGS. 5A and 5B.

FIG. 5C is a diagram representing another orientation of the filter of the embodiment of FIGS. 5A and 5B. Filter 50 and head cross section 58 are shown being approximately perpendicular to their orientation in FIG. 5A. In this orientation, central ray 105 may have a significantly shorter path through head cross section 58 compared to the orientation of FIG. 5A. Rotatable element 53 can be rotated such that central ray 150 has a significantly more attenuating path through filter 50, e.g., a shorter length of hollow region 52 in its path and more attenuation by rotatable element 53. Similarly, outer ray 107 may have a more attenuating path through head cross section 58 in this orientation relative to the orientation of FIG. 5A and a less attenuating path through filter 50. A plurality of orientations can be implemented, e.g., with filter 50 being rotated up to 180 degrees or 360 degrees during an imaging session. Filter 50 can be rotated in sync with gantry rotation, e.g., with rotation of X-ray source 100 and X-ray detector 102 around the imaging subject.

In one embodiment, filter 50 may be positioned, e.g., centered, between 2 cm and 10 cm from X-ray source 100. Filter 50 may, for example, be positioned between 3 cm and 8 cm, 4 cm and 6 cm, or 4.5 cm and 5.5 cm from X-ray source 100, inclusive, or any other integer or non-integer number of centimeters within the enumerated ranges. In this embodiment, the distance between X-ray source 100 and X-ray detector 102 may be between 40 cm and 150 cm, 50 cm and 90 cm, or 60 cm and 80 cm, inclusive, or any integer or non-integer number of centimeters within the enumerated ranges. A center of rotation for the X-ray system, e.g., where an imaging subject may be positioned or centered, may be a point between 10 cm and 140 cm, 20 cm and 80 cm, 30 cm and 70 cm, or 40 cm and 60 cm, inclusive, or any integer or non-integer number of centimeters within the enumerated ranges. For example, in one embodiment of the present invention, X-ray detector 102 may be positioned 70 cm from X-ray source 100, and X-ray source 100, X-ray detector 102, and filter 50 may be rotated about a point that is 50 cm from X-ray source 100.

Filter 50 may have a height, e.g., a dimension into or out of the page in the view of FIGS. 5A through 5C, between 0.5 cm and 10 cm, inclusive. Filter 50 may, for example, have a height between 0.75 cm and 1.25 cm, 1.25 and 1.75 cm, 1.75 cm and 2.25 cm, 2.25 cm and 2.75 cm, or 2.75 cm and 3.25 cm, inclusive, or any other integer or non-integer number of centimeters within or between the enumerated ranges. The diameter, e.g., outer diameter, of rotatable element 53 may be between 1 cm and 8 cm, inclusive. The diameter of rotatable element 53 may be between 1 cm and 2 cm, 2 cm and 3 cm, 3 cm and 4 cm, or 4 cm and 5 cm, inclusive, or any integer or non-integer number of centimeters within or between the enumerated ranges. The diameter of rotatable element 53 may, for example, be 1.5 cm, 1.7 cm, 1.8 cm, 1.9 cm, 2 cm, 2.25 cm, 2.77 cm, or 3.6 cm.

Dimensions of stationary filter element 55 may be tailored to create equal path lengths of X-rays 100 through filter 50. Outer surfaces, e.g., the surface nearest X-ray source 100 and the surface nearest X-ray detector 102, of stationary filter element 55 may, for example, be arc-shaped. Arc-shaped outer surfaces may comprise circular arcs, e.g., centered at the point of X-ray emission from source 100. The distance between these outer surfaces, e.g., the path length of X-rays 100 through filter 50, may be between 1.2 cm and 10 cm, inclusive. The distance between these surfaces may also be between 1.5 cm and 5.5 cm, 2.5 cm and 4.5 cm, or 3 cm and 4 cm, inclusive, or any integer or non-integer number of centimeters within the enumerated ranges. Inner surfaces of stationary filter element 55, e.g., those surfaces nearest rotatable element 53, may follow the shape of rotatable element 53. These surfaces may be configured to allow rotation of element 53 while being positioned within 4 mm, 3 mm, 2 mm, or 1 mm, or 0.5 mm, inclusive, from rotatable element 53. Stationary filter element 55 may, as illustrated in FIGS. 5A through 5C, comprise two or more pieces, e.g., positioned on opposite sides of rotatable element 53, or may comprise a single piece, e.g., having a hole or vacancy to accommodate rotatable element 53.

Dimensions of hollow region 52 may be tailored to a predetermined application or imaging subject. In one embodiment, hollow region 52 can comprise a vacant elliptic cylinder in rotatable element 53. The, e.g., vacant, elliptic cylinder may have a major axis between 0.5 cm and 4.9 cm, including but not limited to between 0.8 cm and 1.2 cm, 1.2 cm and 1.6 cm, 1.6 cm and 2 cm, 2 cm and 2.4 cm, or 2.4 cm and 2.8 cm, inclusive, or any integer or non-integer number of centimeters within the enumerated ranges. The cylinder may have a minor axis between 0.1 cm and 3.8 cm, including but not limited to between 0.3 cm and 0.7 cm, 0.7 cm and 1.1 cm, 1.1 cm and 1.5 cm, 1.5 and 1.9 cm, or 1.9 cm and 2.3 cm, inclusive, or any integer or non-integer number of centimeters within the enumerated ranges. In one embodiment, the minor axis of an elliptic hollow region 52 can be between 50% and 55%, 55% and 60%, 60% and 65%, 65% and 70%, 70% and 75%, 75% and 80%, 80% and 85%, 85% and 90%, or 90% and 95% of the major axis, inclusive, or any other percentage of the major axis.

Figure 6:
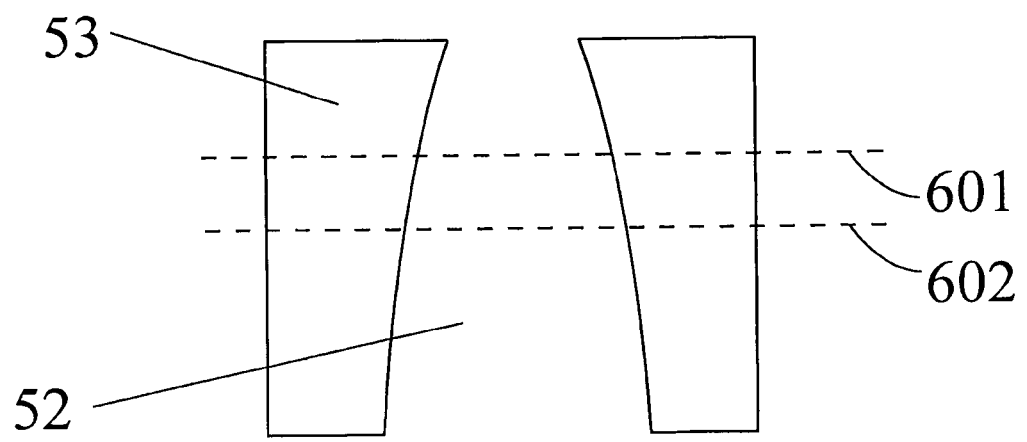
FIG. 6 is a diagram representing a cross section of a filter of one embodiment of the present invention wherein a hollow region in an otherwise attenuating structure varies with height of the structure.

In another embodiment of the present invention, the shape and/or dimensions of hollow region 52 can vary along the height of filter 50, e.g., the direction into or out of the page in the view of FIGS. 5A through 5C. FIG. 6 is a diagram representing a cross section of a filter of one embodiment of the present invention wherein a hollow region in an otherwise attenuating structure varies with height of the structure. For example, in the embodiment of FIG. 6, the dimensions of hollow region 52, e.g., diameter or lengths of major and minor axes, may decrease along the height of rotatable element 53. In this embodiment, the positioning of rotatable element 53 in front of the X-ray source may be flexible to allow the element to be moved, e.g., up or down, in a manner to affect the size of the hollow region in the beam path. For example, if rotatable element 53 were positioned with a lower height 602 centered in the beam path, hollow region 52 could form a relatively larger part of the beam path through the filter than if rotatable element 53 were positioned with an upper height 601 centered in the beam path.

In one embodiment, dimensions of hollow region 52 may vary proportionally, e.g., the ratio of a major axis and minor axis of an elliptical cross section of hollow region 52 may be maintained through the height of rotatable element 53 or a subset of it. In another embodiment, dimensions of hollow region 52 may vary disproportionally, e.g., one axis of an elliptical cross section may decrease faster than another, or one axis may be constant while the other changes.

In this embodiment rotatable element 53, e.g., and filter 50, may have a height, e.g., a vertical dimension in the view of FIG. 6, between 1 cm and 12 cm, inclusive. Rotatable element 53 may, for example, have a height between 5.5 cm and 6.5 cm, 6.5 and 7.5 cm, 7.5 cm and 8.5 cm, 8.5 cm and 9.5 cm, or 9.5 cm and 10.5 cm, inclusive, or any other integer or non-integer number of centimeters within or between the enumerated ranges. Any one of a variety of manners for controlling the positioning of rotatable element 53, e.g., the height at which the element is positioned in the beam path, may be utilized, including but not limited to motorized or non-motorized linear slides, hydraulic or pneumatic actuators, or similar devices.

In one embodiment of the present invention, a positioning height for rotatable element 53, e.g., size of hollow region 52, can be selected based on a measurement or measurements of the imaging subject acquired prior to X-ray imaging. For example, a measurement of a visible light image, a laser scan or laser measurement, or similar measurement can be made to acquire one or more dimensions of the imaging subject.

In another embodiment of the present invention, one of a predetermined set of positioning heights can be selected based on an alternative criterion, including but not limited to age, gender, height, weight, or similar metrics, e.g., of a human imaging subject. In another embodiment, a preliminary low-dose X-ray scan of the imaging subject, e.g., a scout scan, can be taken without a filter in place or with a non-customized filter in place, and an attenuation map derived from this scout scan utilized to select and appropriate positioning of rotatable element 53.

In another embodiment of the present invention, rotatable element 53 may be customized for an imaging subject. Rotatable element 53 can, for example, be 3D-printed or otherwise manufactured according to an attenuation map of the imaging subject. An attenuation map of the imaging subject can be acquired, e.g., for a human patient, by a scout scan or a prior CT scan. For example, a patient scheduled to undergo serial CT scans, e.g., such as during a period of radiation therapy treatments, may have a custom rotatable element or adaptive filter manufactured after a first CT scan. This custom element or filter can be inserted in the X-ray beam path for each subsequent CT scan. An attenuation map may also be acquired, e.g., for metrology applications, from simulation or from a scan of a similar part or master workpiece. A custom rotatable element or filter can be inserted in the X-ray beam path for CT scans of a batch of similar workpieces.

In one embodiment of the present invention, adaptive filter 50 can be utilized for dental computed tomography. Filter 50 can be configured to control the dynamic range on detector 102 during computed tomography image of, e.g., the dental structure of a human patient. For example, an oral cavity 56 is indicated in head cross section 58. In one embodiment, hollow region 52 can be ellipsoidal, e.g., having any of the previously described dimensions. In another embodiment, hollow region 52 can have a shape that is exactly or approximately a miniature shape of a human head, e.g., of the predetermined imaging subject. Hollow region 52 can also be any other function of a measured or predetermined attenuation map of head cross section 58.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. An X-ray imaging system comprising:
an X-ray source for generating an X-ray beam;
an X-ray detector for detecting said X-ray beam;
a gantry for rotating said X-ray source and said X-ray detector around an imaging subject; and
an X-ray filter having a rotatable filter element positioned between said X-ray source and said imaging subject configured to rotate around an internal axis during rotation of said X-ray source and X-ray detector wherein an amount of attenuation of said X-ray beam by said rotatable filter element is a function of angular orientation of said rotatable filter element around said internal axis, wherein said X-ray filter further comprises a stationary filter element conforming to outer edges of said rotatable filter element and configured to equalize distances between side of said filter nearest said X-ray source and side of said filter nearest said X-ray detector traveled by X-rays of said X-ray beam.

2. The X-ray imaging system of claim 1 wherein said rotatable element comprises a cylinder of an X-ray attenuating material with a central less attenuating region.

3. The X-ray imaging system of claim 2 wherein shape of said central less attenuating region is an elliptic cylinder.

4. The X-ray imaging system of claim 2 wherein shape of said central less attenuating region is an elliptic cone.

5. The X-ray imaging system of claim 2 wherein said central less attenuating region is hollow.

6. The X-ray imaging system of claim 2 wherein shape of said central less attenuating region is a function of an attenuation map of said imaging subject.

7. The X-ray imaging system of claim 2 wherein said X-ray attenuating material comprises iron.

8. The X-ray imaging system of claim 2 wherein said X-ray attenuating material comprises aluminum.

9. An X-ray filter for X-ray imaging comprising:
a three-dimensional volume of X-ray attenuating material configured to be positioned within 10 cm from an X-ray source and rotated around a central internal axis, wherein said three-dimensional volume is symmetric around said central internal axis;
a less attenuating three-dimensional region within said three-dimensional volume that is asymmetric around said central internal axis; and
a rotator for rotating said three-dimensional volume around said central internal axis.

10. The X-ray filter of claim 9 wherein said three-dimensional volume is a cylinder.

11. The X-ray filter of claim 9 wherein said three-dimensional region has an elliptic cross section.

12. The X-ray filter of claim 9 wherein cross sectional dimensions of said three-dimensional region vary with height of said three-dimensional volume.

13. The X-ray filter of claim 9 wherein shape of said three-dimensional region is tailored to a predetermined imaging subject.

14. The X-ray filter of claim 9 wherein shape of said three-dimensional region is a miniaturized shape of said imaging subject.

15. A method of X-ray imaging comprising:
- positioning a rotatable filter element in an X-ray beam path between an X-ray source and X-ray detector;
- positioning an imaging subject in said X-ray beam path between said rotatable filter element and said X-ray detector in a first relative angular orientation, said first relative angular orientation being relative to said X-ray source and X-ray detector;
- acquiring a first X-ray projection image of said imaging subject with a first amount of attenuation from said rotatable filter element;
- changing said first relative angular orientation by a predetermined angle;
- rotating said rotatable filter element around an internal axis of rotation by said predetermined angle;
- acquiring a second X-ray projection image of said imaging subject with a second amount of attenuation from said rotatable filter element, wherein said second amount of attenuation is different than said first amount of attenuation;
- acquiring a preliminary measurement of said imaging subject; and
- adjusting properties of said rotatable filter element based on said preliminary measurement.

16. The method of claim 15 further comprising:
rotating said X-ray source and said X-ray detector around said imaging subject to change said first relative angular orientation.

17. The method of claim 15 further comprising:
rotating said imaging subject to change said first relative angular orientation.

* * * * *